(12) United States Patent
Feinberg et al.

(10) Patent No.: US 10,751,165 B2
(45) Date of Patent: Aug. 25, 2020

(54) ADJUSTABLE IMPLANT

(71) Applicant: MENTOR WORLDWIDE LLC, Irvine, CA (US)

(72) Inventors: Marc Feinberg, Ringoes, NJ (US); James Fleming, Bethlehem, PA (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 0 days.

(21) Appl. No.: 15/839,321

(22) Filed: Dec. 12, 2017

(65) Prior Publication Data
US 2019/0175330 A1 Jun. 13, 2019

(51) Int. Cl.
*A61F 2/12* (2006.01)

(52) U.S. Cl.
CPC .......... *A61F 2/12* (2013.01); *A61F 2250/001* (2013.01); *A61F 2250/0002* (2013.01); *A61F 2250/0003* (2013.01); *A61F 2250/0004* (2013.01)

(58) Field of Classification Search
CPC ................ A61F 2/12; A61F 2250/0003; A61F 2250/0004; A61F 2/2445; A61F 2/0059; A61F 2002/30537; A61F 2/2442
See application file for complete search history.

(56) References Cited

U.S. PATENT DOCUMENTS

| 146,805 A | 1/1874 | Cox |
|---|---|---|
| 1,091,063 A | 3/1914 | Hutchinson |
| 1,263,798 A | 4/1918 | Otto |
| 3,852,833 A | 12/1974 | Köneke |
| 3,919,724 A | 11/1975 | Sanders et al. |
| 3,934,274 A | 1/1976 | Hartley, Jr. |
| 4,433,440 A | 2/1984 | Cohen |
| 4,615,704 A | 10/1986 | Frisch |
| 4,624,671 A | 11/1986 | Kress |
| 4,643,733 A | 2/1987 | Becker |
| 4,773,908 A | 9/1988 | Becker |

(Continued)

FOREIGN PATENT DOCUMENTS

| DE | 19923183 A1 | 11/2000 |
|---|---|---|
| EP | 1 547 549 A2 | 6/2005 |

(Continued)

OTHER PUBLICATIONS

Extended European Search Report for European Application No. 17158382.6-1664, dated Jul. 27, 2017, 8 pages.

(Continued)

*Primary Examiner* — Seema Mathew
(74) *Attorney, Agent, or Firm* — Etan S. Chatlynne; Roberts Calderon Safran & Cole P.C.

(57) ABSTRACT

An adjustable implant is disclosed herein. The adjustable implant may comprise a shell including membrane and a base and having a first diameter in a plane parallel to the base. A band may be disposed within the shell. The band may have a first end and a second end connected to a spool. The band may be in a round (e.g., elliptical) configuration having a second diameter in the plane that is less than the first diameter. By wrapping the band onto the spool, the diameter of the band may be decreased and the height of the implant may be increased. By unwrapping the band from the spool, the diameter of the band may be increased and the height of the implant may be decreased.

10 Claims, 9 Drawing Sheets

(56) References Cited

U.S. PATENT DOCUMENTS

| | | | |
|---|---|---|---|
| 4,775,379 A | 10/1988 | Fogarty et al. | |
| 4,790,309 A | 12/1988 | Becker | |
| 4,944,749 A | 7/1990 | Becker | |
| 4,969,892 A | 11/1990 | Burton et al. | |
| 4,969,898 A | 11/1990 | Calogero | |
| 4,969,899 A | 11/1990 | Cox, Jr. | |
| 5,019,101 A | 5/1991 | Purkait et al. | |
| 5,181,907 A | 1/1993 | Becker | |
| 5,219,360 A | 6/1993 | Georgiade | |
| 5,507,808 A | 4/1996 | Becker | |
| 5,549,672 A | 8/1996 | Maddock et al. | |
| 5,630,843 A | 5/1997 | Rosenberg | |
| 5,723,006 A | 3/1998 | Ledergerber | |
| 5,776,159 A | 7/1998 | Young | |
| 6,113,569 A | 9/2000 | Becker | |
| 6,183,514 B1 | 2/2001 | Becker | |
| 6,540,702 B1 | 4/2003 | Sarango | |
| 6,755,861 B2 | 6/2004 | Nakao | |
| 7,081,136 B1 | 7/2006 | Becker | |
| 7,615,074 B2 | 11/2009 | Carvallo | |
| 7,762,982 B1 | 7/2010 | Shah | |
| 8,080,057 B2 | 12/2011 | Kronowitz | |
| 8,197,542 B2 | 6/2012 | Becker | |
| 8,202,317 B2 | 6/2012 | Becker | |
| 8,308,630 B2 | 11/2012 | Birk et al. | |
| 8,394,118 B2 | 3/2013 | Jones et al. | |
| 8,398,710 B2 | 3/2013 | Forsell | |
| 9,265,921 B2 | 2/2016 | Korman | |
| 2002/0011497 A1 | 1/2002 | Farris | |
| 2005/0284215 A1 | 12/2005 | Falsetti | |
| 2006/0069403 A1* | 3/2006 | Shalon | A61F 2/12 606/192 |
| 2006/0100578 A1 | 5/2006 | Lieberman | |
| 2006/0161196 A1 | 7/2006 | Widgerow | |
| 2007/0050026 A1 | 3/2007 | Carvalio | |
| 2007/0276478 A1* | 11/2007 | Marmureanu | A61F 2/2445 623/2.11 |
| 2008/0275569 A1 | 11/2008 | Lesh | |
| 2009/0210056 A1* | 8/2009 | Forsell | A61F 2/12 623/8 |
| 2010/0010531 A1 | 1/2010 | Shalon et al. | |
| 2010/0010871 A1 | 1/2010 | Mengerink | |
| 2010/0087843 A1 | 4/2010 | Bertolote et al. | |
| 2010/0108717 A1 | 5/2010 | Szymanski | |
| 2010/0204792 A1* | 8/2010 | Greco | A61F 2/12 623/8 |
| 2010/0211166 A1* | 8/2010 | Miller | A61F 2/2448 623/2.37 |
| 2010/0228347 A1 | 9/2010 | Schuessler | |
| 2010/0324688 A1 | 12/2010 | Doty | |
| 2011/0106249 A1 | 5/2011 | Becker | |
| 2011/0153017 A1 | 6/2011 | McClellan | |
| 2011/0160854 A1 | 6/2011 | Berg et al. | |
| 2011/0160859 A1 | 6/2011 | Doty | |
| 2011/0230845 A1 | 9/2011 | Pascal et al. | |
| 2011/0264213 A1 | 10/2011 | DeMiranda | |
| 2012/0116509 A1 | 5/2012 | Forsell | |
| 2013/0007980 A1 | 1/2013 | Worker et al. | |
| 2013/0013063 A1 | 1/2013 | Del Vechio | |
| 2013/0013084 A1 | 1/2013 | Birk | |
| 2013/0079807 A1 | 3/2013 | Korman | |
| 2013/0237915 A1 | 9/2013 | Barrelli | |
| 2013/0245758 A1 | 9/2013 | Chitre et al. | |
| 2013/0341353 A1 | 12/2013 | Harris | |
| 2014/0031619 A1 | 1/2014 | Moon | |
| 2014/0100656 A1 | 4/2014 | Namnoum et al. | |
| 2014/0156001 A1 | 6/2014 | Davodian | |
| 2014/0200396 A1 | 7/2014 | Lashinski et al. | |
| 2014/0236210 A1* | 8/2014 | Payne | A61B 90/02 606/192 |
| 2015/0038976 A1 | 2/2015 | Roschak et al. | |
| 2016/0045312 A1* | 2/2016 | Braido | A61F 2/24 623/2.37 |
| 2016/0228603 A1 | 8/2016 | Nguyen et al. | |
| 2016/0250017 A1 | 9/2016 | McClellan | |
| 2016/0310711 A1 | 10/2016 | Luxon et al. | |
| 2017/0079737 A1* | 3/2017 | Jones | A61F 2/12 |
| 2017/0127929 A1 | 5/2017 | Schutt et al. | |
| 2017/0165025 A1 | 6/2017 | Payne et al. | |
| 2017/0333179 A1 | 11/2017 | Forsell | |
| 2018/0153684 A1 | 6/2018 | Van Heugten et al. | |
| 2018/0200714 A1 | 7/2018 | Viovy et al. | |
| 2018/0279889 A1 | 10/2018 | Lee | |
| 2019/0091001 A1 | 3/2019 | Forsell | |
| 2019/0111206 A1 | 4/2019 | Forsell | |
| 2019/0223971 A1 | 7/2019 | Payne et al. | |

FOREIGN PATENT DOCUMENTS

| | | |
|---|---|---|
| EP | 2453839 B1 | 3/2014 |
| WO | 9504561 A1 | 2/1995 |
| WO | 2016003718 A1 | 1/2016 |

OTHER PUBLICATIONS

International Search Report and Written Opinion for International Application No. PCT/IB2018/056354, dated Nov. 16, 2018, 12 pages.

Becker Expander/Mammary Prostheses (Reconstruction Adjunct Study) Mentor, 2002 <http://www.mentorwwllc.com/Documents/Becker.pdf>.

* cited by examiner

ADJUSTABLE IMPLANT

CROSS-REFERENCE TO CO-PENDING APPLICATION

This application is a counterpart of U.S. patent application Ser. No. 15/693,965, filed Sep. 1, 2017, and Ser. No. 15/807,017, filed Nov. 8, 2017, both of which are incorporated by reference in their entirety.

FIELD

The subject matter disclosed herein relates to breast implants for use in a subject.

BACKGROUND

Tissue expanders are used to assist in stretching skin of a subject to provide a tissue pocket or capsule having an appropriate size to accommodate a permanent implant, such as a breast implant. In typical usage, the tissue expander is implanted into a subject to help prepare the subject to receive a permanent breast implant. The tissue expander may be expanded by introducing additional material therein, e.g., saline, until the desired size of the pocket or capsule is achieved, at which point the tissue expander may be removed. A permanent breast implant may then be implanted into the subject.

Certain tissue expanders may be used as an adjustable breast implant, such as the Becker Expander/Mammary Prostheses manufactured by Medtronic of Irvine, Tex. This adjustable implant utilizes a fill tube through which saline may be introduced or removed from the implant to change the implant's size. Thus, the adjustable implant may be used to change the size of the capsule. Once the desired size of the capsule is achieved, the fill tube may be removed from the implant, thereby rendering the implant non-adjustable. The implant may remain in the capsule.

SUMMARY

An adjustable implant is disclosed herein. The adjustable implant may comprise a shell including a membrane and a base and having a first diameter in a plane parallel to the base. A band may be disposed within the shell. A mechanism including a spool may also be disposed within the shell. The band may have a first end and a second end. The first end may be connected to the spool. The second end may also be connected to the spool. The band may be in a round (e.g., elliptical) configuration having a second diameter in the plane that is less than the first diameter.

In some embodiments, the mechanism may include a gear that is coupled to the spool, a first pawl having a first pin, a second pawl having a second pin, a first clip having a first groove and a first hole, and a second clip having a second groove and a second hole. The first hole may be mated about the first pin and the second hole may be mated about the second pin. The mechanism may also include an advancement actuator having a first post mated to the first groove. The mechanism may also include a release actuator having a second post mated to the second groove. In some embodiments, the first pawl contacts a first tooth of the gear and the second pawl contacts a second tooth of the gear. A lever may also be included that has a first end connected to the first pawl and a second end disposed proximate the second post.

In some embodiments, the mechanism may include a motor coupled to the spool. The motor may include a battery, such as a rechargeable battery. The motor may also include a communication module, e.g., a wireless-communication module.

The band in the implant may be adjustable. That is, the second diameter may be decreased by wrapping the band onto the spool and the second diameter may be increased by unwrapping the band from the spool. In some embodiments, the implant includes a second or inner membrane within the membrane, and the band may be disposed about the inner membrane.

The implant may be used according the following exemplary method and variations. The diameter of the band may be decreased and the height of the implant may be increased. Further, the diameter of the band may be increased and the height of the implant may be decreased. The implant may include a spool connected to a first end of the band such that the band may be wrapped onto the spool to decrease the diameter of the band and the band may be unwrapped from the spool to increase the diameter of the band. In some variations, an advancement actuator may be depressed to rotate the spool in a first direction, which causes the band to wrap onto the spool. In some variations, a release actuator may be depressed to rotate the spool in a second direction, which causes the band to unwrap from the spool.

For those embodiments that include a motor, the method may include a step of activating the motor to rotate the spool and wrap the band thereon. The motor may be remotely activated via a remote control, such as a Smartphone.

BRIEF DESCRIPTION OF THE DRAWINGS

While the specification concludes with claims which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
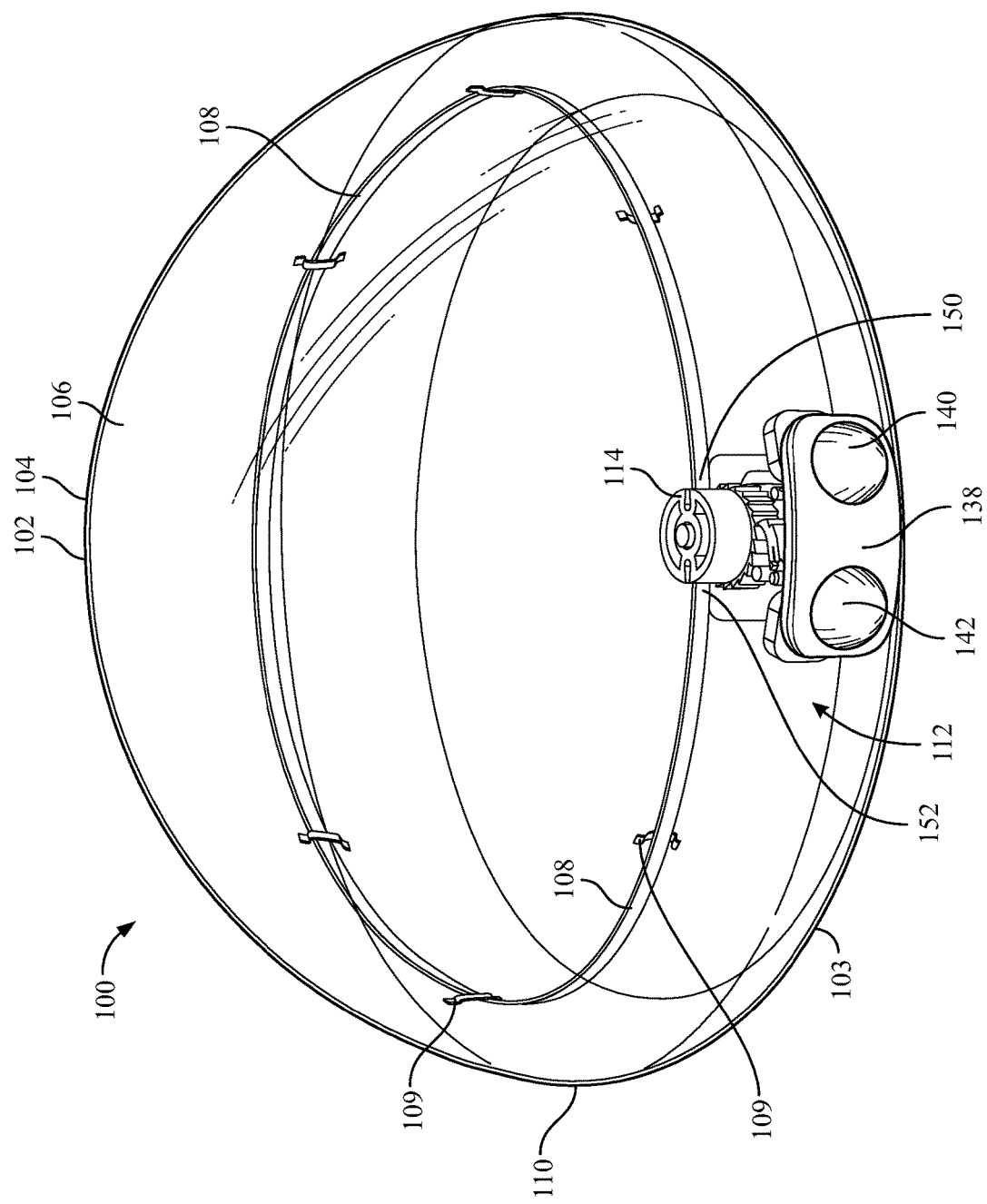
FIG. 1 depicts a perspective view of an adjustable implant having a spool mechanism.
Figure 2:
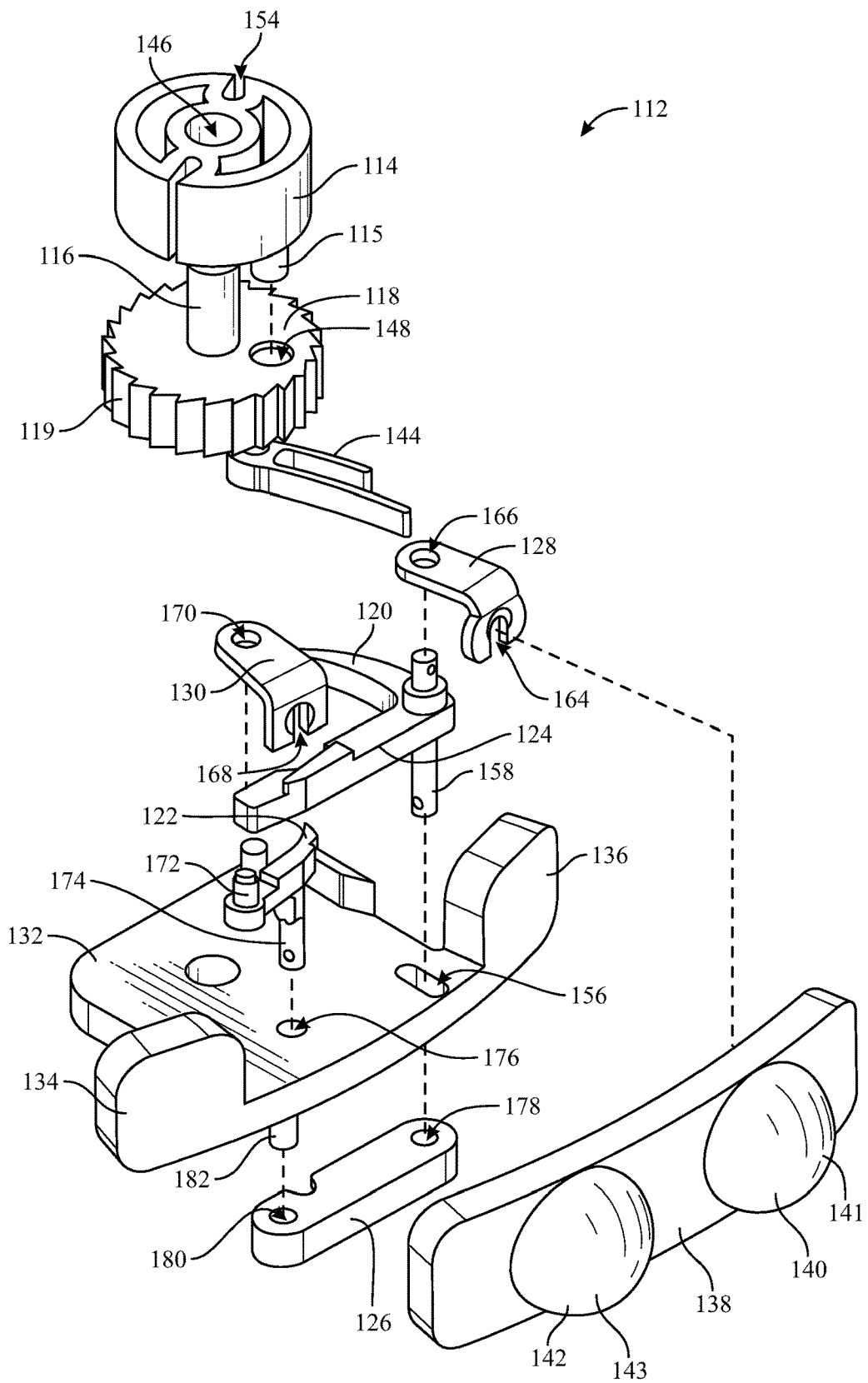
FIG. 2 depicts an exploded view of the spool mechanism of FIG. 1.
Figure 3:
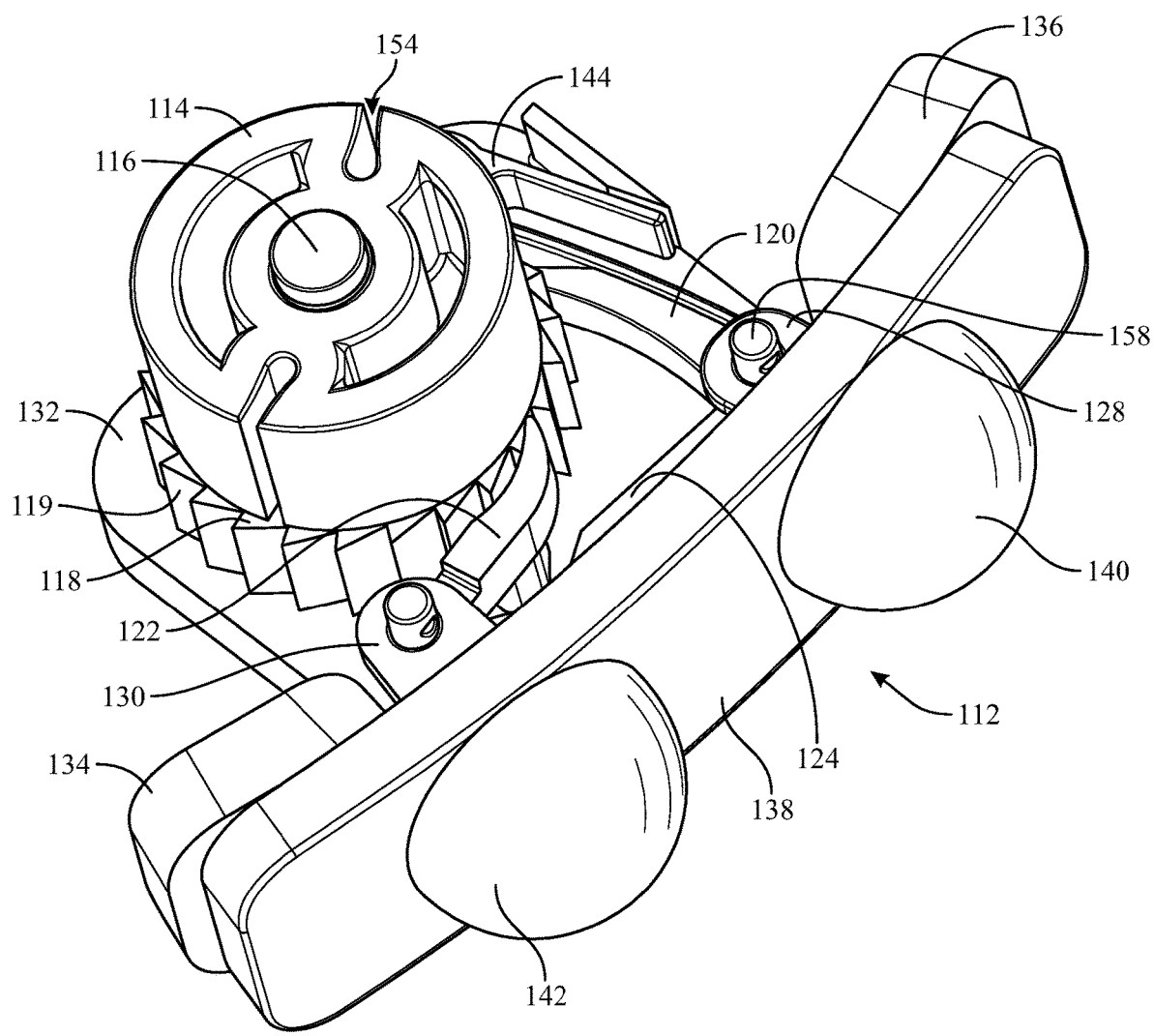
FIG. 3 depicts a perspective view of the spool mechanism of FIG. 1.
Figure 4:
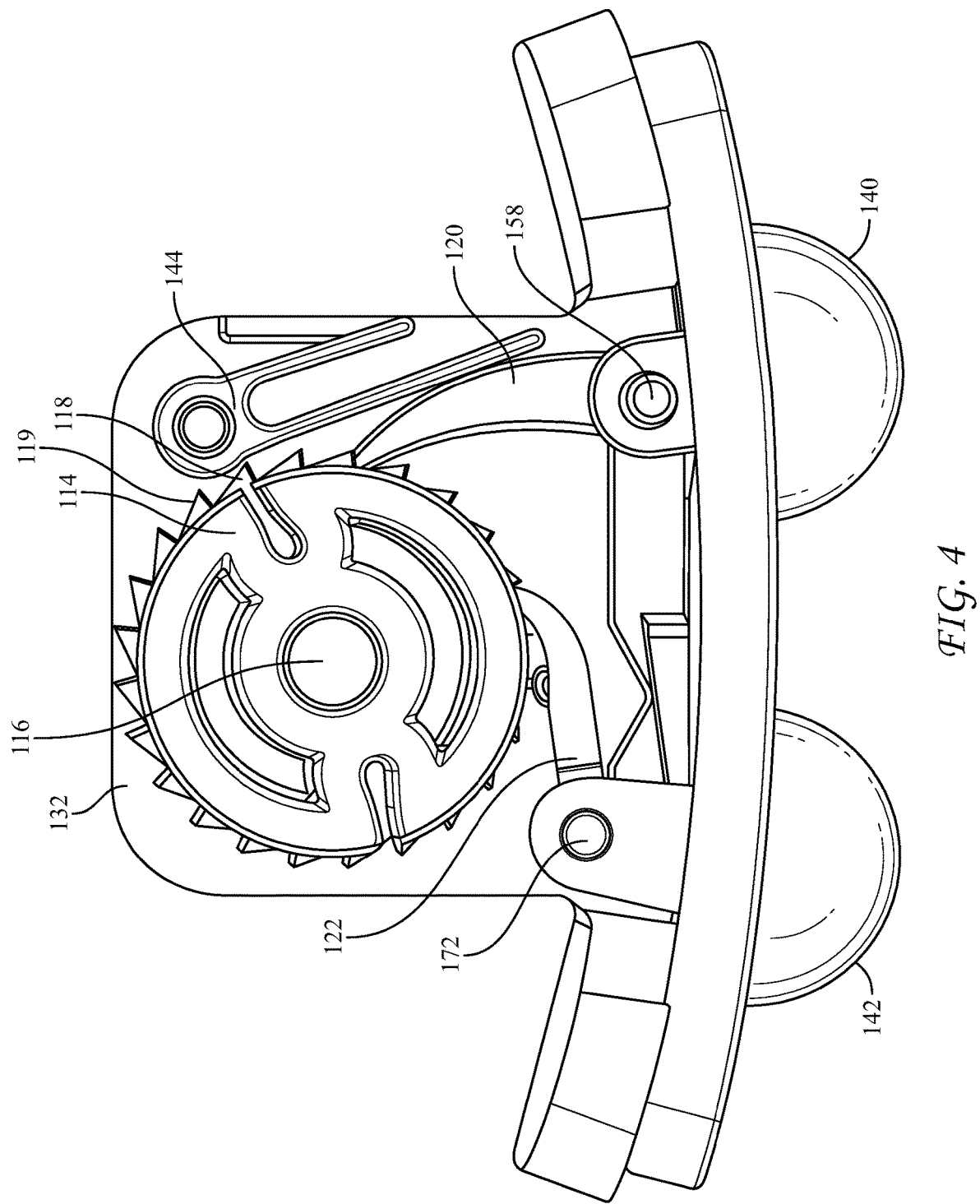
FIG. 4 depicts a top view of the spool mechanism of FIG. 1.
Figure 5:
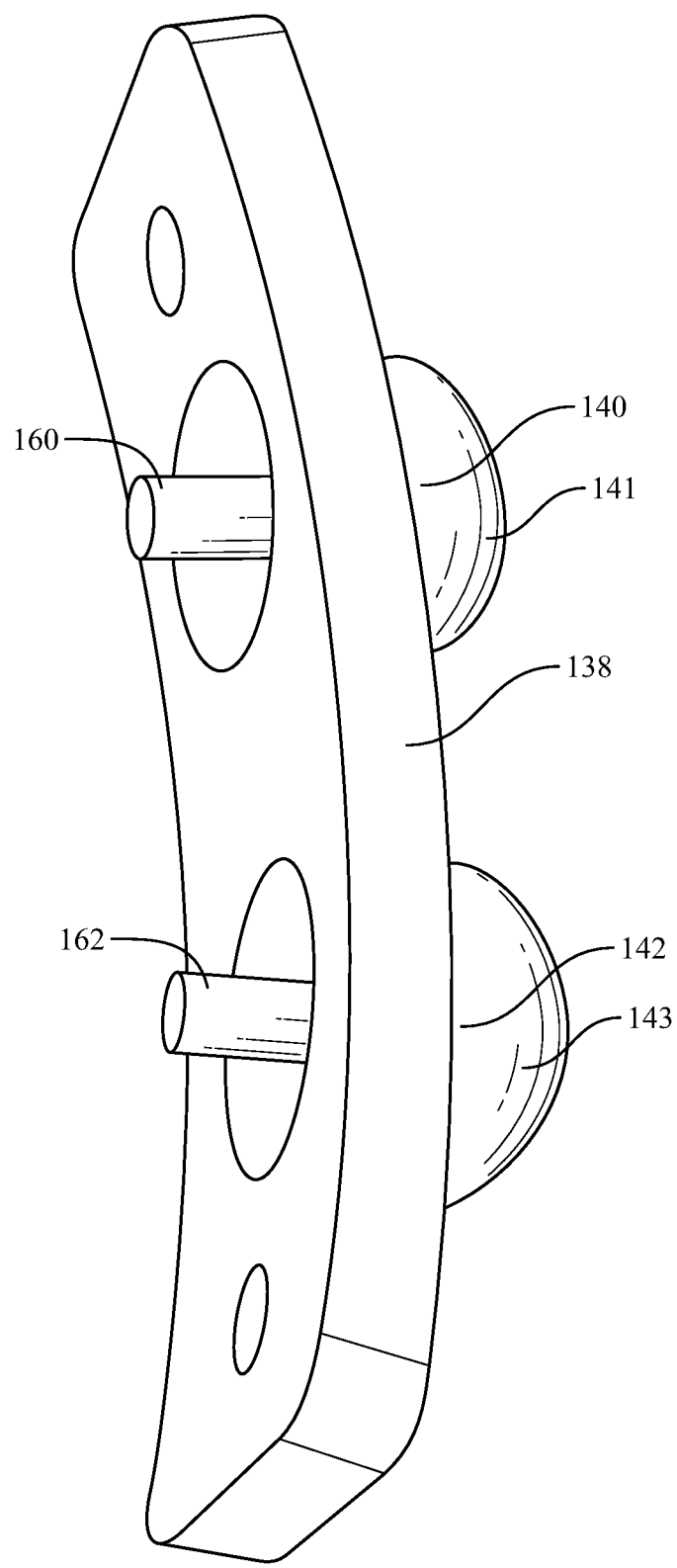
FIG. 5 depicts a perspective view of an actuator body of the spool mechanism of FIG. 1.
Figure 6:
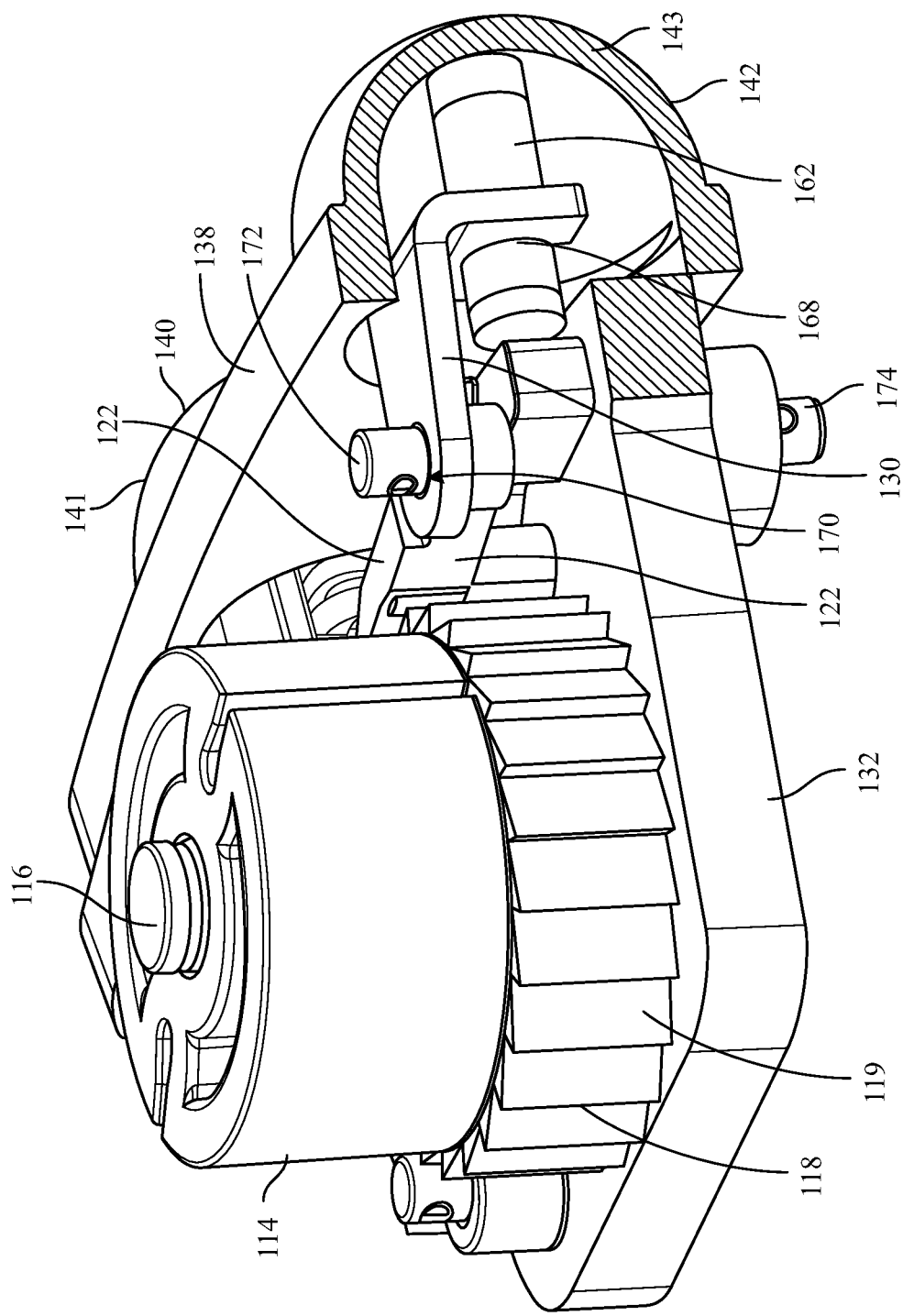
FIG. 6 depicts a section view of the spool mechanism of FIG. 1.

FIG. 1 is a representation of an exemplary embodiment of the present subject matter, i.e., adjustable implant 100. Adjustable implant 100 includes a shell 102, which includes a base 103. Shell 102 includes a shell membrane 104 that may be fabricated from any resilient and/or stretchable material used to fabricate conventional implants, particularly breast implants. For example, elastomeric silicones, such as silicone rubber, may be used to fabricate shell membrane 104. Shell 102 may be filled with a material 106 to maintain a desired form and prevent shell membrane 104 from collapsing and deforming under its own weight. In some embodiments, shell 102 has the form of a conventional breast implant, which is the form of shell 102 reflected in the figures. Further, material 106 may provide compliance and/or resiliency when shell membrane is subject to external forces generated by, e.g., foreign objects or a subject's anatomy. The material 106 may be, e.g., an elastomer, such as silicone rubber, a silicone gel, or a liquid, such as saline.

Adjustable implant 100 additionally includes a flexible band 108 made of e.g., elastic, rubber, or plastic. Alternatively, it may be a fluoropolymer, such as Teflon, which may provide certain advantages over other alternatives including low friction and bacterial resistance. Band 108 may have a round configuration, including, but not limited to an elliptical (including circular) configuration, ovular configuration, annular configuration, disk configuration, or spherical configuration. Further, it may be oriented such that it may be parallel or nearly parallel to base 103 of implant 100. The configuration of band 108 includes a diameter θ that is less than the diameter of a circumferential portion 110 of shell 102 that is coplanar with band 108. In certain embodiments, the plane including circumferential portion 110 and band 108 also includes the maximum diameter of implant 100. That is, band 108 is disposed in a plane where implant 100 is widest. Loops 109 may be provided within material 106 in a round or elliptical configuration. Loops 109 may additionally be attached to an inner surface of shell membrane 104. Band 108 may be disposed within loops 109 in a manner similar to a belt in belt loops on a pair of pants. In some embodiments, a sheath (not shown) for band 108 may be provided. In these embodiments, band 108 may be disposed within the sheath and the sheath may be disposed through loops 109. The sheath may be fabricated from any material that is also suitable for fabricating band 108, such as Teflon.

Implant 100 may have a maximum diameter ranging between approximately three inches and seven inches. In some embodiments, the maximum diameter θ of band 108 is approximately 0.2 inches to 1 inch less than the maximum diameter of implant 100. Band 108 may be a thin strip having a thickness of between approximately 0.03 inches and 0.15 inches. Band 108 may have a height of between approximately 0.25 inches and 1 inch.

Diameter θ of band 108 may be decreased or increased. When θ is decreased, band 108 squeezes material 106, which causes a corresponding increase in height of shell 102. Further, in those embodiments including loops 109, band 108 displaces loops 109, which may further facilitate squeezing material 106 by evenly distributing the constrictive forces upon material 106 caused by reducing diameter θ. Further, in those embodiments where loops 109 are attached or bonded to the inner surface of shell membrane 104, shell membrane 104 may further distribute the constrictive forces. When θ is increased, band 108 releases the portion of material 106 that was being squeezed, which causes a corresponding decrease in the height of shell 102. In some embodiments, the height of shell 102 may be increased by between approximately 0.2 inches and 2 inches. In certain embodiments, the height of shell 102 may be increased by approximately 0.5 inches.

Various embodiments of an adjustable implant are described herein, each including a mechanism disposed within the adjustable implant for driving a spool, or a "spool mechanism," onto which a band may be wrapped. For example, as shown in FIG. 1, a spool mechanism 112 may be embedded within material 106 of implant 100 and coupled to band 108 for changing the diameter θ of band 108. Spool mechanism 112 may be controlled by a subject in which implant 100 is implanted (as opposed to requiring manipulation by a health care professional).

Spool mechanism 112 is detailed in FIGS. 2-6. With initial reference to FIG. 2, which is an exploded view of mechanism 112, and FIG. 3, which is an assembly view of mechanism 112, mechanism 112 includes various components, including a spool 114, a rod 116, a gear 118, a first pawl 120, a second pawl 122, a guide spring 144, a first lever 124, a second lever 126, a first clip 128, a second clip 130, a plate 132 having tabs 134 and 136, and an actuator body 138 on which are disposed advancing actuator 140 and release actuator 142.

Band 108 is attached to spool 114. The attachment may be effectuated by an adhesive or via mechanical means (e.g., cleats) securing it within channel 154. Thus, as spool 114 is rotated band 108 may be wrapped onto spool 114 or unwrapped from it. Band 108 may be attached to spool 114 at both its first end 150 and second end 152 as shown in the figures. Alternatively, in some embodiments, band 108 may be attached to spool 114 at only one of its ends 150 or 152. The other end may be attached to, e.g., a stationary feature of mechanism 112, e.g., a post disposed proximate spool 114 and/or gear 118.

Spool 114 may be mated to gear 118 by rod 116, which mates within hole 146. Further, spool 114 and gear 118 may be rotatably coupled to each other. For example, spool 114 may include a post 115 that mates into hole 146. Alternatively, rod 116 and spool 114 may be keyed to each other by including tongue and groove features upon rod 116 and within hole 146. Accordingly, as gear 118 rotates, spool 114 rotates, causing band 108 to wrap onto or wrap off of spool 114.

Gear 118 may be rotated or advanced in a counter-clockwise direction by displacing a first pawl 120 against a gear tooth 119, which causes band 108 to wrap onto spool 114, which reduces diameter θ. Due to the resilient nature of implant 100, and particularly shell membrane 104 and material 106, reduction of diameter θ causes a spring-type tension within band 108. Accordingly, ratchet functionality may be employed to help prevent this tension from unwinding band 108 from spool 114. A second pawl 122 may thus be included that contacts another gear tooth 119 to resist clock-wise motion of gear 118. In various embodiments, not shown, a portion of gear 118 may lack gear teeth.

First pawl 120 and second pawl 122 may be operated by a user via actuator body 138, which includes advancing actuator 140 and release actuator 142. First pawl 120 traverses a path delineated by guide spring 144 and a slot 156 in plate 132 that retains a pin 158 of first pawl 120. Depression of advancing actuator 140 displaces first pawl 120 against a gear tooth 119, which causes gear 118 to rotate counter clockwise. Upon release of advancing actuator 140, first pawl 120 returns to its original position. Pawl 120 may return to its original position under a spring force imparted by advancing actuator 140. In some embodiments, advancing actuator may be a combination of an elastomeric bulb 141 and post 160. Post 160 may mate with first pawl 120. As reflected in the figures, post 160 connects to a groove 164 of first clip 128 and hole 166 of clip 128 mates about pin 158 of first pawl 120. Thus, first pawl 120 is advanced upon depression of advancing actuator 140 and retracted upon release of advancing actuator 140. Second pawl 122 maintains the position of gear 118 as advancing actuator 140 returns first pawl 120 to its original position.

Depression of release actuator 142 disengages second pawl 122 from gear 118, thus allowing gear 118 to rotate clockwise. In some embodiments, including those reflected in the figures, first pawl 120 my also be rotated away from gear 118 to remove its restriction to movement of gear 118. Specifically, first lever 124 may include a first end connected to first pawl 120 and a second end disposed proximate post 162 of release actuator 142. When post 162 is displaced against the second end of first lever 124 upon depression of release actuator 142, the first end of first lever 124 displaces first pawl 120 away from gear 118 such that first pawl 120 does not prevent clockwise rotation of gear 118. Accordingly, if band 108 is wound onto spool 114, band 108 will unwind from spool 114 because any resistance to rotation provided by second pawl 122, and in some embodiments, first pawl 120, has been removed. Similar to advancing actuator 140 in some embodiments, release actuator 142 may be a combination of an elastomeric bulb 143 and post 162. Post 162 may mate with second pawl 122. As best seen with references to FIGS. 2 and 6, post 162 connects to a groove 168 of clip 130 and hole 170 of clip 130 mates about pin 172 of second pawl 122. Another pin 174 of second pawl 122 mates into hole 176 of plate 132. Thus, as release actuator 142 is depressed, post 162 pushes clip 130 to advance pin 172, which causes clockwise rotation of second pawl 122 about pin 174, disengaging second pawl 122 from gear 118. The reverse occurs upon release of release actuator 142. That is, due to its elastomeric resilient nature, post 162 returns to its original configuration and pulls clip 130 to withdraw pin 172, which causes counter-clockwise rotation of second pawl 122 about pin 174, re-engaging second pawl 122 against gear 118.

Lever 126 may be included to assist in maintaining alignment between first pawl 120 and gear 118. For example, pin 158 may also mate with hole 178 of second lever 126 in addition to slot 156 of plate 132. Hole 180 of second lever 126 may mate about stationary post 182 of plate 132. Thus lever 126 may rotate about a fixed point defined by post 182, which helps maintain alignment of the other moving parts in mechanism 112.

Mechanism 112 also includes tabs 134 and 136. Tabs 134 and 136 may be features of plate 132. Tabs 134 and 136 may be useful for attaching actuator body 138 to plate 132 with proper alignment to control mechanism 112. Further, tabs 134 and 136 assist in maintaining the position of mechanism 112 within shell 102 by resisting forces applied to actuator body 138, particularly forces applied to advancing actuator 140 and release actuator 142. In some embodiments not shown, actuator body 138 may be positioned near to the bottom of shell 102, i.e., proximate base 103.

In some embodiments, mechanism 112 is oriented within implant 100 such that advancing actuator 140 and release actuator 142 are disposed proximate membrane 104 of shell 102. In some embodiments, advancing actuator 140 and release actuator 142 may contact an inner surface of membrane 104. Accordingly, a user in whom implant 100 is implanted may actuate actuators 140 and 142 by pressing her skin proximate the desired actuator.

Depression of advancing actuator 140 causes spool 114 to rotate counter clockwise, which in turn causes band 108 to wrap thereon. As band 108 wraps onto spool 114, diameter θ of band 108 decreases, which causes a corresponding increase in height of shell 102. Conversely, depression of release actuator 142 causes spool 114 to rotate clockwise, which in turn allows band 108 to unwrap therefrom. As band 108 unwraps from spool 114, diameter θ of band 108 increases, which causes a corresponding decrease in height of shell 102.

A cover or sheath (not shown) may be disposed upon or about spool mechanism 112 to protect it from outside interference. For example, the moving parts of spool mechanism 112, e.g., spool 114, gear 118, first pawl 120, and second pawl 122, should be covered to prevent material 106 from interfering with these components, which could potentially cause the mechanism to malfunction.

Figure 7A:
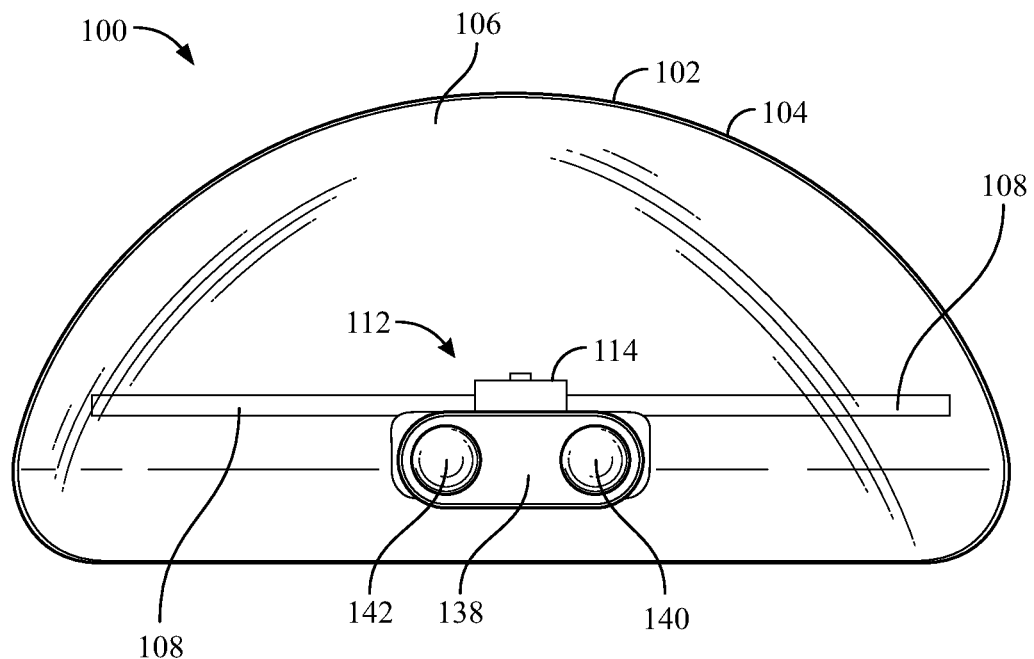
FIG. 7A depicts a front view of the adjustable implant of FIG. 1 having an original profile.
Figure 7B:
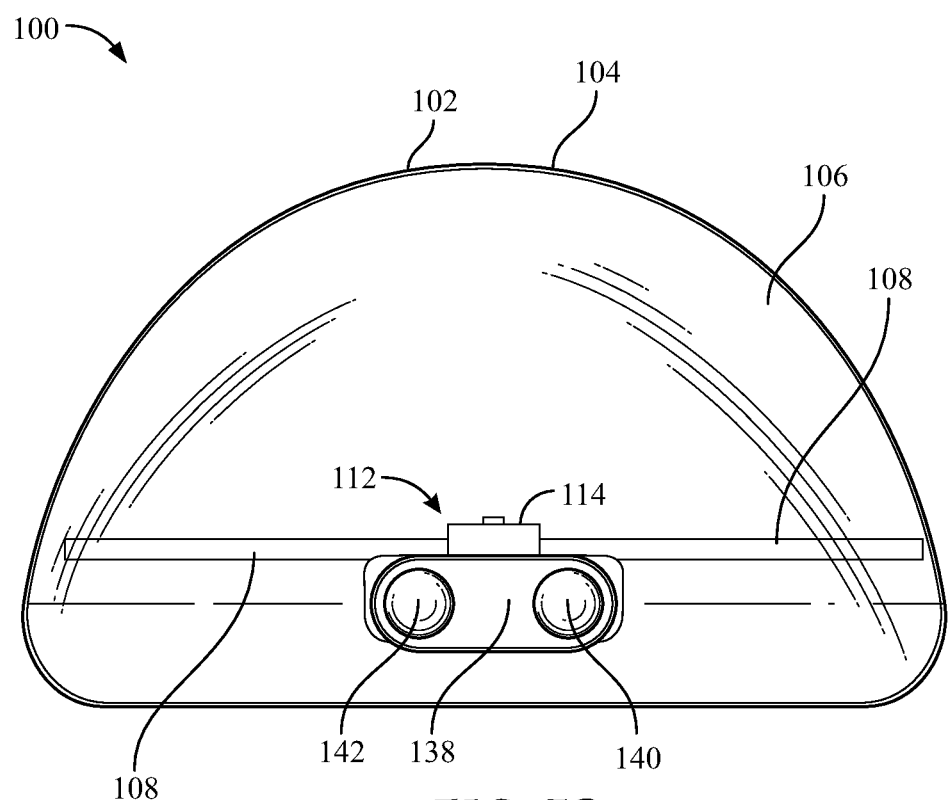
FIG. 7B depicts a front view of the adjustable implant of FIG. 1 having a heightened profile.

FIGS. 7A and 7B reflect two different profiles of adjustable implant 100. The profile of implant 100 may be changed from an original profile, reflected in FIG. 7A, to a heightened profile reflected in FIG. 7B. This change in profile is effected by reducing diameter θ of band 108 using mechanism 112. The original profile may be recovered by enlarging the diameter θ of band 108 using mechanism 112. Intermediate profiles (not shown) may also be achieved by reducing diameter θ less than is required to achieve the heightened profile. Accordingly, a subject may change the profile of implant 100 to her desired preference by using mechanism 112 to change diameter θ of band 108.

It should be appreciated by those of skill in the art that the foregoing description of mechanism 112 is exemplary, as are the descriptions of mechanisms 212 and 312 below. Alternative embodiments of these mechanisms may be designed that could achieve diameter changes in band 108, particularly after one of skill in the art has reviewed the present disclosure. Such design changes are considered to be within the scope of the present disclosed subject matter.

Implant 100 may be used according to the following exemplary method. First, implant 100 may be provided. Second, advancing actuator 140 may be depressed, which causes pawl 120 to rotate gear 118, which in turn rotates spool 114 causing band 108 to wrap thereon. Third, repeated depressions of advancing actuator 140 causes repeated rotations of gear 118 and spool 114, further wrapping band 108 onto spool 114. In some embodiments, approximately fifteen depressions of actuator 140 results in a maximum length of band 108 being wrapped onto spool 114. As noted above, in some embodiments, a portion of gear 118 may lack gear teeth. Thus, repeated depressions of actuator 140 will cause first pawl 120 to reach the portion of gear 118 that lacks teeth, thereby preventing further rotation of gear 118 and further wrapping of band 108 onto spool 114. Fourth, the diameter θ of band 108 is decreased and the height of implant 100 is increased.

Fifth, release actuator 142 may be depressed. This step may occur when any length of band is wrapped onto spool 114, e.g., when band 108 is substantially wrapped thereon following, e.g., ten depressions of advancing actuator 140. Depressing release actuator 142 causes second pawl 122 to rotate away from gear 118. In some embodiments, particularly those where pawl 120 rests against gear 118, depressing release actuator 142 also causes first pawl 120 to rotate away from gear 118. Thus, depressing actuator 142 disengages pawls 120 and 122 from gear 118, allowing it to rotate freely. Sixth, under the spring-type forces in band 108 imparted therein by winding band 108 onto spool 114, band 108 unwinds from spool 114. Band 108 continues to unwind from spool 114 until either release actuator 142 is released or band 108 unwraps entirely from spool 114. Seventh the diameter θ of band 108 is increased and the height of implant 100 is decreased.

The foregoing method may be applied by a subject in whom implant 100 is implanted to change the height of the implant. Correspondingly, she may change the projection of her breast. For example, the subject may begin with implant 100 having a configuration in which band 108 has a maximum diameter θ such that the height of shell 102 is a minimum. To increase the projection of her breast, the subject may depress advancing actuator 140 at least one time to decrease the diameter θ of band 108 and increase the height of shell 102. For example, if the subject would like her breast to be a little bigger, the subject may depress advancing actuator 140 approximately two to approximately four times, which, in some embodiments, may cause the height of shell 102 to increase about a quarter to one third from its minimum height toward its maximum height. Alternatively, if the subject would like her breast to be substantially bigger, the subject may palpitate advancing actuator 140 about fifteen to twenty times, which, in some embodiments, may cause the height of shell 102 to increase to its maximum height.

After the subject has enlarged her breast, she may decide that she would like to shrink her breast. To shrink her breast, she may depress release actuator 142 until her breast has reached the size she desires. However, if she shrinks her breast too much, she may enlarge it to the desired size by palpitating advancing actuator 140. In this manner, she may "fine tune" the projection of her breast. Further, she may do so whenever she desires to change the size of her breast because the adjustability of implant 100 is a permanent feature of the implant that cannot be removed. This is so because adjustable implant 100 is entirely self-contained, like a conventional permanent implant, but unlike conventional tissue expanders or the Becker Expander/Mammary Prostheses. No fluids, liquids, or other materials are introduced or removed from within the boundary defined by shell membrane 104 in order to change the profile of implant 100.

Figure 8:
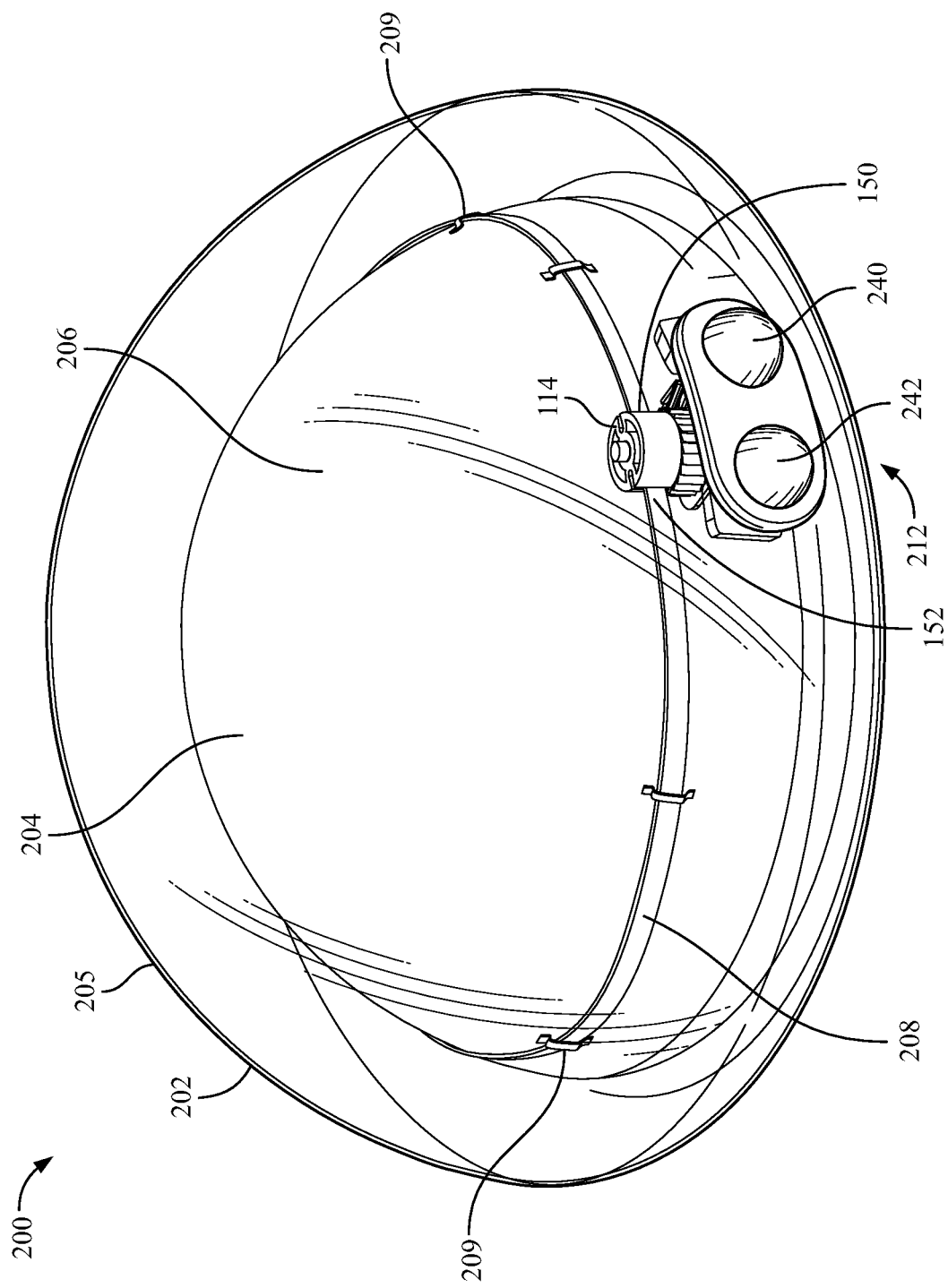
FIG. 8 depicts a perspective view of an alternate embodiment of an adjustable implant.

FIG. 8 shows an alternate embodiment of an adjustable implant. Implant 200 includes a shell 202 having two membranes, an inner or first membrane 204 and an outer or second membrane 205 that surrounds inner membrane 204. Both inner membrane 204 and outer membrane 205 are filled with material 206. Band 208 is disposed about and proximate to inner membrane 204. In some embodiments, loops 209 may be circumferentially distributed about and attached to inner membrane 204 such that band 208 is further disposed within loops 209. Spool mechanism 212 may be used to change a diameter of band 208 to change the profile of inner membrane 204, which in turn changes the profile of outer membrane 205 and the overall profile of implant 200. In some embodiments, mechanism 212 is disposed between inner membrane 204 and outer membrane 205 such that advancing actuator 240 and release actuator 242 are proximate an inner surface of outer membrane 205.

Figure 9:
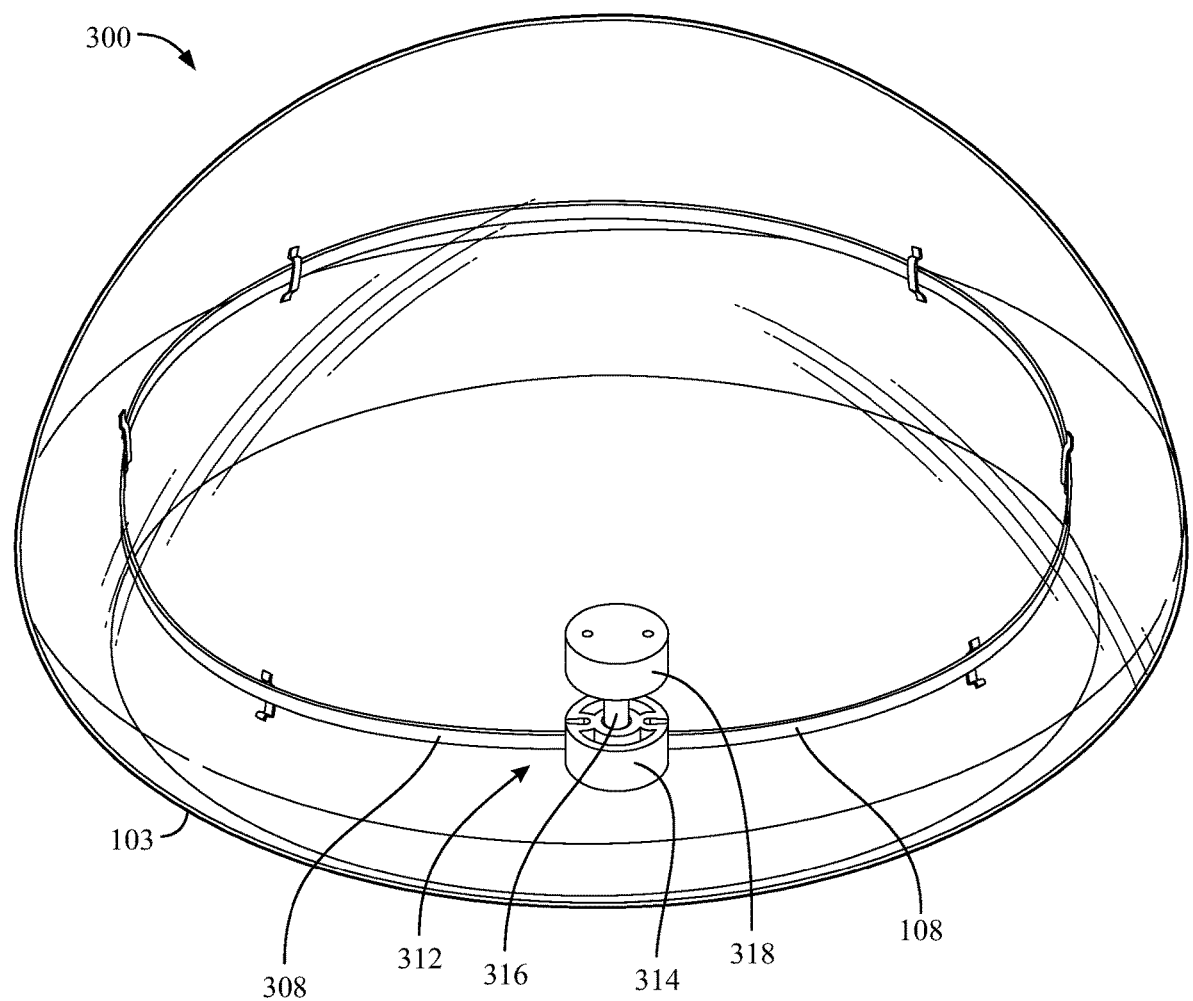
FIG. 9 depicts a perspective view of another alternate embodiment of an adjustable implant.

In alternate embodiments, the spool mechanism may include a motor driven by electromechanical energy. For example, FIG. 9 shows an adjustable implant 300 that includes a spool mechanism 312. Instead of the mechanical gears included in the foregoing embodiments, spool mechanism 312 includes a motor 318, which may be, e.g., a dc motor, a stepper motor, servo motor, or piezoelectric motor. A piezoelectric motor may avoid magnetic issues posed by MRIs. Motor 318 may include a shaft 316 to which a spool 314 may be attached. In some embodiments, spool 314 and shaft 316 may be a single component. In other embodiments, shaft 316 may serve as a spool. In those embodiments including an electromechanical motor, the profile of implant 300 may be changed using band 308 in a manner similar to implants 100 and 200 using bands 108 and 208. However, an electromechanical spool mechanism provides various potential advantages over a pure mechanical mechanism.

First, electromechanical spool mechanism 312 may be more accurate and less likely to malfunction than a spool mechanism with a gear and pawls, such as spool mechanism 112 and 212. Second, electromechanical mechanism 312 may be more reliable because it includes fewer parts and should subject to fewer user-based manipulations (e.g., different users may depress actuators with varying amounts of force). Third, electromechanical mechanism 312 may be automated. Thus, it may be programmed at one time to wrap and unwrap band 308 from spool 314 at other times. Fourth, electromechanical mechanism 314 may include or be attached to a wireless antenna such that it may be remotely controlled by a user operating a remote control, which may assist a user in operating her implant discretely and avoids potential manipulation through clothing. The remote control may include a storage medium into which various preset sizes of an adjustable implant may be set by the user such that the user need not set the size of the implant while watching the implant. Instead, she may simple select a preset size, which may further assist changing the size of the implant discretely. In various embodiments, programming and remote controlling may be accomplished via a remote device or control, including a Smartphone operating an appropriate application in communication with electromechanical mechanism 312.

Electromechanical spool mechanism 312 may be actuated by a powered storage device, such as a battery, which may be rechargeable. The battery may be recharged wirelessly, e.g., by inductive charging or wireless charging. Ideally, electromechanical implant 312 prohibits operation when a battery is near empty to avoid an implant being unable to reach a desired size until after the battery is recharged.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. An adjustable implant, comprising:
   a shell including a base and having a first diameter in a plane parallel to the base, the shell further including a membrane;
   a band disposed within the shell in a round configuration and having a second diameter in the plane that is less than the first diameter, the band having a first end and a second end; and a mechanism disposed within the shell, the mechanism including:
  a spool;
  a gear coupled to the spool;
  a first pawl having a first pin;
  a second pawl having a second pin;
  a first clip having a first groove and a first hole mated about the first pin;
  a second clip having a second groove and a second hole mated about the second pin;
  an advancement actuator including a first post mated to the first groove; and
  a release actuator including a second post mated to the second groove,
  wherein the first end of the band is connected to the spool.

2. The adjustable implant of claim 1, wherein the second end of the band is connected to the spool.

3. The adjustable implant of claim 1, wherein the first pawl contacts a first tooth of the gear.

4. The adjustable implant of claim 3, wherein the second pawl contacts a second tooth of the gear.

5. The adjustable implant of claim 3 further comprising a lever having a first end and a second end, the first end connected to the first pawl and the second end disposed proximate the second post.

6. The adjustable implant of claim 1, wherein the mechanism further comprises:
  a motor coupled to the spool.

7. The adjustable implant of claim 6, wherein the motor includes a rechargeable battery.

8. The adjustable implant of claim 7, wherein the motor includes a wireless-communication module.

9. The adjustable implant of claim 8, wherein the round configuration is an elliptical configuration.

10. The adjustable implant of claim 1, further comprising an inner membrane surrounded by the membrane, wherein the band is disposed about the inner membrane.

* * * * *